US011599525B2

(12) United States Patent
Bastide et al.

(10) Patent No.: US 11,599,525 B2
(45) Date of Patent: Mar. 7, 2023

(54) DATA RECOVERY DURING INFRASTRUCTURE OUTAGE EVENTS

(71) Applicant: International Business Machines Corporation, Armonk, NY (US)

(72) Inventors: Paul R. Bastide, Ashland, MA (US); Matthew E. Broomhall, Goffstown, NH (US); Robert E. Loredo, North Miami Beach, FL (US)

(73) Assignee: International Business Machines Corporation, Armonk, NY (US)

( * ) Notice: Subject to any disclaimer, the term of this patent is extended or adjusted under 35 U.S.C. 154(b) by 271 days.

(21) Appl. No.: 16/852,634

(22) Filed: Apr. 20, 2020

(65) Prior Publication Data

US 2021/0326329 A1    Oct. 21, 2021

(51) Int. Cl.
*G06F 7/00* (2006.01)
*G06F 16/23* (2019.01)
(Continued)

(52) U.S. Cl.
CPC ......... *G06F 16/2372* (2019.01); *G16H 10/60* (2018.01); *G16H 40/20* (2018.01)

(58) Field of Classification Search
CPC .................................................. G06F 16/2372
(Continued)

(56) References Cited

U.S. PATENT DOCUMENTS 7,213,005 B2 * 5/2007 Mourad ............... G06Q 20/382
705/64
7,587,368 B2 * 9/2009 Felsher ............... G06F 21/6245
705/52

(Continued)

FOREIGN PATENT DOCUMENTS

EP          3080742 A1 * 10/2016
EP          3080742 A1 * 10/2016

OTHER PUBLICATIONS

Walter et al. "Technologies for Extracting Full Value from the Electronic Patient Record"; Hawaii International Conference on System Sciences; 1999.*

(Continued)

*Primary Examiner* — Daniel A Kuddus
(74) *Attorney, Agent, or Firm* — Edell, Shapiro & Finnan, LLC (57) ABSTRACT

A computer system provides access to data during an outage. A plurality of data records are analyzed to identify entities whose data records indicate that a service is within an upcoming time period. A data resource is generated for each identified entity and the data resources for the identified entities are stored within a repository, wherein each data resource includes data obtained from a data record of a corresponding identified entity that is relevant to the service. The data resource of an identified entity is accessed with a corresponding recovery key during the outage and transform the data resource into one or more printable forms. The one or more printable forms are transmitted to one or more providers of the service. Embodiments of the present invention further include a method and program product for providing access to data during an outage in substantially the same manner described above.

17 Claims, 4 Drawing Sheets

(51) Int. Cl.
*G16H 10/60* (2018.01)
*G16H 40/20* (2018.01)

(58) Field of Classification Search
USPC .................................. 707/609, 636, 666, 674
See application file for complete search history.

(56) References Cited

U.S. PATENT DOCUMENTS

| | | | | |
|---|---|---|---|---|
| 7,805,377 | B2* | 9/2010 | Felsher | G06Q 10/10 |
| | | | | 705/64 |
| 8,380,630 | B2* | 2/2013 | Felsher | G06F 21/6227 |
| | | | | 705/50 |
| 8,515,926 | B2* | 8/2013 | Goldenberg | G06F 16/2471 |
| | | | | 707/696 |
| 8,600,895 | B2* | 12/2013 | Felsher | G06Q 30/0283 |
| | | | | 705/50 |
| 9,760,681 | B2 | 9/2017 | Douglass | |
| 2002/0002468 | A1* | 1/2002 | Spagna | G06T 1/0021 |
| | | | | 713/193 |
| 2006/0053077 | A1* | 3/2006 | Mourad | G06Q 20/3821 |
| | | | | 707/E17.116 |
| 2007/0075135 | A1* | 4/2007 | Dertinger | G06Q 10/087 |
| | | | | 235/382.5 |
| 2007/0078687 | A1* | 4/2007 | Dertinger | G06Q 20/40 |
| | | | | 705/3 |
| 2007/0143148 | A1* | 6/2007 | Koi | G06Q 40/08 |
| | | | | 705/3 |
| 2008/0172737 | A1* | 7/2008 | Shen | G16H 10/60 |
| | | | | 726/21 |
| 2009/0287837 | A1* | 11/2009 | Felsher | G06F 21/6245 |
| | | | | 709/229 |
| 2013/0060579 | A1* | 3/2013 | Yu | H04L 63/06 |
| | | | | 705/3 |
| 2013/0147622 | A1* | 6/2013 | LaLonde | G16H 10/60 |
| | | | | 340/539.12 |
| 2013/0159021 | A1* | 6/2013 | Felsher | G16H 10/60 |
| | | | | 705/3 |
| 2014/0222684 | A1* | 8/2014 | Felsher | G16H 10/60 |
| | | | | 705/50 |
| 2015/0163206 | A1* | 6/2015 | McCarthy | H04L 63/104 |
| | | | | 726/4 |
| 2015/0310188 | A1* | 10/2015 | Ford | H04L 63/0428 |
| | | | | 726/28 |
| 2016/0147944 | A1* | 5/2016 | Douglass | G06F 21/31 |
| | | | | 705/51 |
| 2017/0085668 | A1 | 3/2017 | Gasser et al. | |
| 2017/0142076 | A1* | 5/2017 | Ford | H04L 63/061 |
| 2018/0082024 | A1* | 3/2018 | Curbera | G16H 40/63 |
| 2018/0144095 | A1* | 5/2018 | Fellowes | G16H 10/60 |
| 2019/0318815 | A1 | 10/2019 | Bandurski et al. | |

OTHER PUBLICATIONS

E. Larsen, et al., "Continuing Patient Care During Electronic Health Record Downtime", Applied Clinical Informatics Journal, 10.03 (2019): 495-504, May 2019, 16 pages.

* cited by examiner

DATA RECOVERY DURING INFRASTRUCTURE OUTAGE EVENTS

BACKGROUND

1. Technical Field

Present invention embodiments relate to database systems, and more specifically, to providing access to data during infrastructure outage events.

2. Discussion of the Related Art

In the field of database management, natural or human-induced infrastructure outages can render data inaccessible. A data center can be brought offline by a power outage, or a ransomware attack can prevent access to information. Critical services such as health care can be disrupted by an infrastructure outage. For example, a health care provider may not be able to access patient schedules or longitudinal patient records, negatively impacting any patients in need of medical services.

SUMMARY

According to one embodiment of the present invention, a computer system provides access to data during an outage. A plurality of data records are analyzed to identify entities whose data records indicate that a service is within an upcoming time period. A data resource is generated for each identified entity and the data resources for the identified entities are stored within a repository, wherein each data resource includes data obtained from a data record of a corresponding identified entity that is relevant to the service. The data resource of an identified entity is accessed with a corresponding recovery key during the outage and transform the data resource into one or more printable forms. The one or more printable forms are transmitted to one or more providers of the service. Embodiments of the present invention further include a method and program product for providing access to data during an outage in substantially the same manner described above. Thus, present invention embodiments improve data management in a manner that greatly increases the number of entities that can be provided a service during the interim in which an outage renders data records inaccessible.

Various other embodiments of the present invention will now be discussed. In some embodiments, the one or more printable forms are automatically transmitted to a printing queue designated by each provider in response to the data records becoming inaccessible. Thus, providers can rapidly transition to a temporary paper-based system during an outage. In some embodiments, each data resource indicates a mapping of data included in the data resource to fields of the one or more printable forms, and wherein each data resource is transformed according to the mapping. Thus, data resources can be transformed into printable forms without requiring any external instructions or specialized software. In some embodiments, the entities are further identified based on a criticality of the service being provided to each entity. Thus, the size of a backup can remain manageable without impacting entities in critical need of services. In some embodiments, the one or more printable forms are selected based on the service being provided to the identified entity. Thus, forms are specifically tailored to include entity data that is useful and/or necessary in order to provide the particular service to an entity. In some embodiments, additional data for the identified entity is received from a provider after the service has been provided, and the data record of the identified entity is updated using the additional data. Thus, once a database system recovers from an outage, providers can easily transition back to using electronic data records. In some embodiments, the service includes a medical service, and each entity is a patient. Thus, patients will receive better health care and experience improved outcomes. In some embodiments, the data included in each data resource is encrypted and the corresponding recovery key is a temporary key. Thus, data access can be provided in a manner that complies with regulatory requirements and/or ensures the privacy of entity data.

BRIEF DESCRIPTION OF THE DRAWINGS

Generally, like reference numerals in the various figures are utilized to designate like components.

DETAILED DESCRIPTION

Present invention embodiments relate to database systems, and more specifically, to providing access to, or recovering, data during infrastructure outage events. An infrastructure outage event can include any natural disaster or human-induced disruption that causes data in a database to become inaccessible. For example, a hurricane can interrupt the power supply to a data center, a ransomware attack can encrypt a database, or a hard drive can fail. While a disaster recovery plan can eventually restore data, critical services may be disrupted in the meantime. For example, when a health care clinic cannot access patient data records or schedules, patients might not receive timely and/or appropriate treatment.

Present invention embodiments maintain a cache of critical information that enables providers to continue providing services during times in which data relevant to the services is inaccessible. In particular, data records of entities are analyzed to identify any entities who are scheduled to receive a service within a selected period of time. Entities who are likely to receive a service may also be identified. The data records of these entities are processed to extract any data that is necessary or useful for the service being provided, and a package for each entity is generated and provided to a trusted recovery repository. This process is repeated often to ensure that the repository is updated, and in the event of an infrastructure outage, the stored data packages can be transformed into forms that are readable and useful to a provider. Thus, a provider can transition from electronic to paper documentation during the interim in which the outage renders data records inaccessible.

By identifying and selectively preserving data that is most likely to be necessary during an outage, present invention embodiments reduce the amount of computing resources (e.g., storage, processing, and memory resources) required to maintain, recover, and deploy data. Thus, present invention embodiments improve data management in a manner that greatly increases the number of entities, such as patients, that can be treated by a provider during an infrastructure outage event. In use cases such as health care, present invention embodiments can improve patient outcomes and reduce or eliminate any costs associated with losing access to patient data or operating without an appointment schedule.

Various other embodiments of the present invention will now be discussed. In some embodiments, the one or more printable forms are automatically transmitted to a printing queue designated by each provider in response to the data records becoming inaccessible. Thus, providers can rapidly transition to a temporary paper-based system during an outage. In some embodiments, each data resource indicates a mapping of data included in the data resource to fields of the one or more printable forms, and wherein each data resource is transformed according to the mapping. Thus, data resources can be transformed into printable forms without requiring any external instructions or specialized software. In some embodiments, the entities are further identified based on a criticality of the service being provided to each entity. Thus, the size of a backup can remain manageable without impacting entities in critical need of services. In some embodiments, the one or more printable forms are selected based on the service being provided to the identified entity. Thus, forms are specifically tailored to include entity data that is useful and/or necessary in order to provide the particular service to an entity. In some embodiments, additional data for the identified entity is received from a provider after the service has been provided, and the data record of the identified entity is updated using the additional data. Thus, once a database system recovers from an outage, providers can easily transition back to using electronic data records. In some embodiments, the service includes a medical service, and each entity is a patient. Thus, patients will receive better health care and experience improved outcomes. In some embodiments, the data included in each data resource is encrypted and the corresponding recovery key is a temporary key. Thus, data access can be provided in a manner that complies with regulatory requirements and/or ensures the privacy of entity data.

It should be noted that references throughout this specification to features, advantages, or similar language herein do not imply that all of the features and advantages that may be realized with the embodiments disclosed herein should be, or are in, any single embodiment of the invention. Rather, language referring to the features and advantages is understood to mean that a specific feature, advantage, or characteristic described in connection with an embodiment is included in at least one embodiment of the present invention. Thus, discussion of the features, advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages will become more fully apparent from the following drawings, description and appended claims, or may be learned by the practice of embodiments of the invention as set forth hereinafter.

Figure 1:
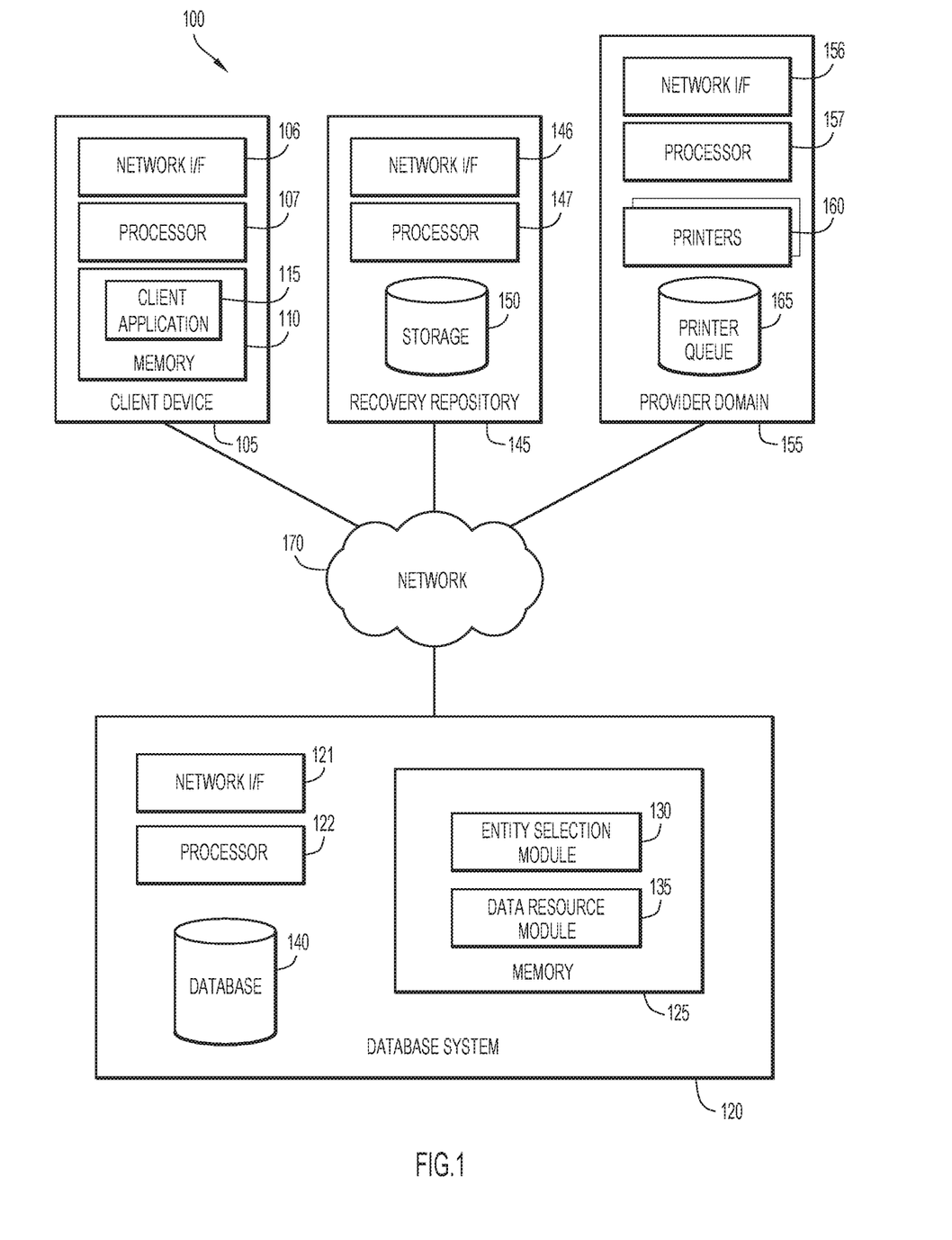
FIG. 1 is a block diagram depicting a computing environment for providing access to data during infrastructure outages in accordance with an embodiment of the present invention.

Present invention embodiments will now be described in detail with reference to the Figures. FIG. 1 is a block diagram depicting a computing environment 100 for providing access to data during infrastructure outages in accordance with an embodiment of the present invention. As depicted, computing environment 100 includes a client device 105, a database system 120, a recovery repository 145, a provider domain 155, and a network 170. It is to be understood that the functional division among components of computing environment 100 have been chosen for purposes of explaining present invention embodiments and is not to be construed as a limiting example.

Client device 105 includes a network interface (I/F) 106, at least one processor 107, and memory 110 that includes a client application 115. Client device 105 may include a laptop computer, a tablet computer, a netbook computer, a personal computer (PC), a desktop computer, a personal digital assistant (PDA), a smart phone, a thin client, or any programmable electronic device capable of executing computer readable program instructions. Network interface 106 enables components of client device 105 to send and receive data over a network, such as network 170. In general, client device 105 enables a user to access data records stored in a database, such as database 140, and to obtain data needed to provide services when the database becomes inaccessible. Client device 105 may include internal and external hardware components, as depicted and described in further detail with respect to FIG. 4.

Client application 115 may include one or more modules or units to perform various functions of present invention embodiments described below. Client application 115 may be implemented by any combination of any quantity of software and/or hardware modules or units, and may reside within memory 110 of client device 105 for execution by a processor, such as processor 107.

Client application 115 may enable a user of client device 105 to retrieve data used to provide a service. Client application 115 can submit requests for data to database system 120, and receive data for presentation to a user. For example, a health care provider may review a patient's medical history, demographic information, medical images, and the like. Additionally, client application 115 may enable a user to submit data to database system 120, such as an update to a patient's record.

Client application 115 enables a user of client device 105 to obtain necessary data for entities when a primary database is inaccessible. For example, if database system 120 becomes unreachable, client application 115 can obtain entity data from recovery repository 145. In some embodiments, a user of client device 105 submits a recovery key to recovery repository 145, which transforms entity data into a readable format that can be reviewed on client device 105 and/or printed to create a hard copy. In some embodiments, entity data is transformed into a readable format and/or printed automatically in response to data records of database 140 becoming inaccessible. In addition, the recovered data may be used to re-build or restore the primary database, or a new database may be generated with the recovered information to restore or replace the primary database.

Database system 120 includes a network interface (I/F) 121, at least one processor 122, and memory 125. Memory 125 may include an entity selection module 130, and a data resource module 135. Database system 120 may include a laptop computer, a tablet computer, a netbook computer, a personal computer (PC), a desktop computer, a personal digital assistant (PDA), a smart phone, a thin client, or any programmable electronic device capable of executing computer readable program instructions. Network interface 121 enables components of database system 120 to send and receive data over a network, such as network 170. In general, database system 120 and its modules maintain data records for entities, and identify particular entity data that is backed up in case an infrastructure outage impacts database system 120. Database system 120 may include internal and external hardware components, as depicted and described in further detail with respect to FIG. 4.

Entity selection module 130 and data resource module 135 may include one or more modules or units to perform various functions of present invention embodiments described below. Entity selection module 130 and data resource module 135 may be implemented by any combination of any quantity of software and/or hardware modules or units, and may reside within memory 125 of database system 120 for execution by a processor, such as processor 122.

Entity selection module 130 analyzes data records of entities in database 140 to identify entities that are scheduled to receive a service and/or entities that are likely to receive a service within a defined period of time. The time period may be defined by a provider or administrator of database system 120, and can be any amount of time, such as one day, one week, two weeks, one month, and the like. For example, if the time period is one month, entity selection module 130 will identify any entities who are scheduled to receive, or likely to receive, one or more services at some point within the next month.

Entity selection module 130 analyzes data records of database 140 to identify entities having appointments with a provider that are scheduled to occur during the defined period of time. An entity's data record may explicitly indicate a date and time for a future service. For example, a patient's data record might indicate that the patient is scheduled to receive physical therapy at a particular date and time. In some embodiments, entity selection module 130 can infer that an entity has an appointment based on other data in the entity's data record, such as regularly occurring prior appointments, services that are scheduled to terminate or expire, and the like. For example, if an entity receives a service every six months and the entity last received the service approximately five months ago, entity selection module 130 can determine that the entity is likely to receive the service again in the next month. As another example, if a patient is prescribed a medication and the patient's dosage schedule indicates that the patient will finish the prescription at some point during the selected time period, entity selection module 130 can determine that the patient is likely to make an appointment for a medical service.

Entity selection module 130 can analyze data records to identify entities likely to receive services within a selected time period based on the cadence of frequency of appointments for a specific group or class of entities to which a particular entity may belong. For example, a male who is between 65 and 70 years of age and who has had a hip fracture may have an average of nine appointments over the recovery process. Thus, entity selection module 130 can identify entities as likely to receive services by applying a set of predefined rules or selection criteria to the data records of entities.

In some embodiments, entity selection module 130 employs a classification model that is trained using conventional or other machine learning techniques to identify entities who are likely to have appointments within the selected time period. For example, data records of entities who were either provided services, or not provided services, within the selected time period can be labeled and used as training data to train a classification model. Feature selection can be performed on the features (e.g., attributes or variables) of the data records to identify a subset of features that are predictive of upcoming service appointments, and the classification model can be trained based on those identified features. For example, a classification model may classify entities as likely to have future appointments based on their data record values for the features of age, medical diagnoses or procedures (e.g., based on $10^{th}$ revision of International Statistical Classification of Diseases and Related Health Problems (ICD-10) codes in the patient's record), body mass index, and the like.

In some embodiments, entity selection module 130 removes or omits certain entities despite the entities' data records indicating that the entities will receive, or are likely to receive, a service within the defined time period. In particular, entity selection module 130 can evaluate entities based on the criticality or urgency of the services being provided to the entities and/or other values in the entities' data records. For example, entity selection module 130 may not select patients who have upcoming appointments for services that are elective rather than necessary. Entity selection module 130 may prioritize entities based on criticality for inclusion when a selection has a defined maximum size. For example, if only one hundred data records may be selected due to limited storage capacity or other constraints, entity selection module 130 may select all of the records of patients scheduled for critical services (e.g., 70 patient records), and may complete the selection by additionally selecting as many records of patients scheduled for elective services as possible (e.g., 30 patient records), which can be sorted based on criticality. Entity selection module 130 may employ a rules-based system to determine criticality of entities. For example, a conventional or other triage scale (e.g., Emergency Severity Index) can be applied to patient records to determine criticality.

Data resource module 135 generates a data resource for each entity selected by entity selection module 130, and uploads data resources to a trusted recovery repository, such as recovery repository 145. Data resources generated by data resource module 135 include some or all of the data of an entity's data record, and may conform to a particular standard or format. In some embodiments, data resources store data according to a Fast Healthcare Interoperability Resources (FHIR) standard. A separate data resource may be generated for each entity and/or for each separate appointment of each entity.

A data resource may include a longitudinal patient record, demographic data, contact information, insurance information, and/or billing information. A data resource may also include contextual metadata describing the context of a service, such as upcoming appointments for the patient, anticipated appointments, and the service being provided. A data resource may also include instructions to transform data in the data resource into a readable and/or printable form. In particular, a data resource may include a mapping of fields of the data resource to fields in one or more forms. Data resources may also include one or more form templates that are used to generate forms by populating fields of a form with data of the data resource according to the mapping. In some embodiments, each data resource includes a unique code for each entity, such as a matrix barcode (e.g., a quick response (QR) code), a universally unique identifier (UUID) or other entity-specific descriptor.

Data resource module 135 may identify particular data in an entity's data record that is relevant to the service being provided to the entity. Each service may be associated with a predetermined subset of data of the entity's data record. For example, medical images of a patient obtained by x-ray radiography or magnetic resonance imaging may be included in a data resource generated for a radiological appointment, but may be omitted from a data resource generated for a dermatological appointment.

Data resource module 135 may encrypt data in a data resource and generate a recovery key that can decrypt the data. Recovery keys may be temporary or session keys. A same recovery key may decrypt multiple data resources, or a separate recovery key may be generated for each data resource. For example, a recovery key may be provider-specific and may be used to decrypt all of the data resources of entities associated with a single provider. Alternatively, a single recovery key may decrypt all of the data resources of a particular entity. Thus, recovery keys can be appointment-specific, entity-specific, or provider-specific.

Data resource module 135 may generate data resources according to a predefined schedule and/or may generate data resources on an ad hoc basis. For example, data resources may be generated each day to ensure that recent data will be accessible during an infrastructure outage event. Alternatively, data resources may be generated each time a data record is modified. Entity selection module 130 may perform entity selection before each scheduled data resource generation job. Data resource module 135 transmits generated data resources to a trusted recovery repository, such as recovery repository 145. In some embodiments, data resources are submitted to the trusted recovery repository using an encrypted protocol such as secure file transfer protocol (SFTP). In some embodiments, data resources are submitted using an application programming interface (API). For example, data resources may be sent to a Kafka topic that is write-only.

Database 140 may include any non-volatile storage media known in the art. For example, database 140 can be implemented with a tape library, optical library, one or more independent hard disk drives, or multiple hard disk drives in a redundant array of independent disks (RAID). Similarly, data in database 140 may conform to any suitable storage architecture known in the art, such as a file, a relational database, an object-oriented database, and/or one or more tables. In some embodiments, database 140 may store data records of entities, which can include any data collected about entities by any collection mechanism, any combination of collected information, and any information derived from analyzing collected information. A provider may access database 140 in order to obtain data from one or more data records and/or provide data to create, update, or modify data records.

Recovery repository 145 includes a network interface (I/F) 146, at least one processor 147, and storage 150. Recovery repository 145 may be a database system and may include any programmable electronic device capable of executing computer readable program instructions. Network interface 146 enables components of recovery repository 145 to send and receive data over a network, such as network 170. In general, recovery repository 145 stores data, including data resources generated by database system 120, and enables providers to access stored data. Recovery repository 145 may be physically located in a location that is offsite from database system 120, so that recovery repository 145 is unlikely to be affected by an infrastructure outage event that would also affect database system 120. In some embodiments, processor 147 of recovery repository 145 executes instructions included in data resources to generate forms that are made accessible to one or more providers. Recovery repository 145 may include internal and external hardware components, as depicted and described in further detail with respect to FIG. 4.

Storage 150 may include any non-volatile storage media known in the art. For example, storage 150 can be implemented with a tape library, optical library, one or more independent hard disk drives, or multiple hard disk drives in a redundant array of independent disks (RAID). Similarly, data in storage 150 may conform to any suitable storage architecture known in the art, such as a file, a relational database, an object-oriented database, and/or one or more tables. Storage 150 stores data resources that are provided by database system 120. In some embodiments, storage 150 automatically deletes, marks for deletion, or writes over data resources based on a timeout value of each data resource. For example, a data resource may be deleted on or after the time and date of the scheduled service for which the data resource was created.

Provider domain 155 includes a network interface (I/F) 156, at least one processor 157, printers 160, and a printer queue 165. In various embodiments, provider domain 155 may include one or more programmable electronic devices capable of executing computer readable program instructions and associated with a provider. Network interface 146 enables components of provider domain 155 to send and receive data over a network, such as network 170. Provider domain 155 may include devices in a provider's network, such as client device 105.

Printers 160 may include any printing devices capable of creating persistent representations of graphics and/or text, such as paper documents. Printers 160 may include toner-based printers, inkjet printers, thermal printers, and the like, and may be incorporated into computing devices such as facsimile machines or photocopiers. Provider domain 155 may include one or more printers 160. Printers 160 may print documents that are provided to printer queue 165, which is a reserved memory or disk space that stores output designated for printing. In some embodiments, printers 160 and printer queue 165 together provide a secure print release environment in which documents are held in a printer queue 165 until a user interacts with a particular printer to begin printing documents associated with the user.

Network 170 may include a local area network (LAN), a wide area network (WAN) such as the Internet, or a combination of the two, and includes wired, wireless, or fiber optic connections. In general, network 170 can be any combination of connections and protocols known in the art that will support communications between client device 105, database system 120, recovery repository 145, and/or provider domain 155 via their respective network interfaces in accordance with embodiments of the present invention.

Figure 2:
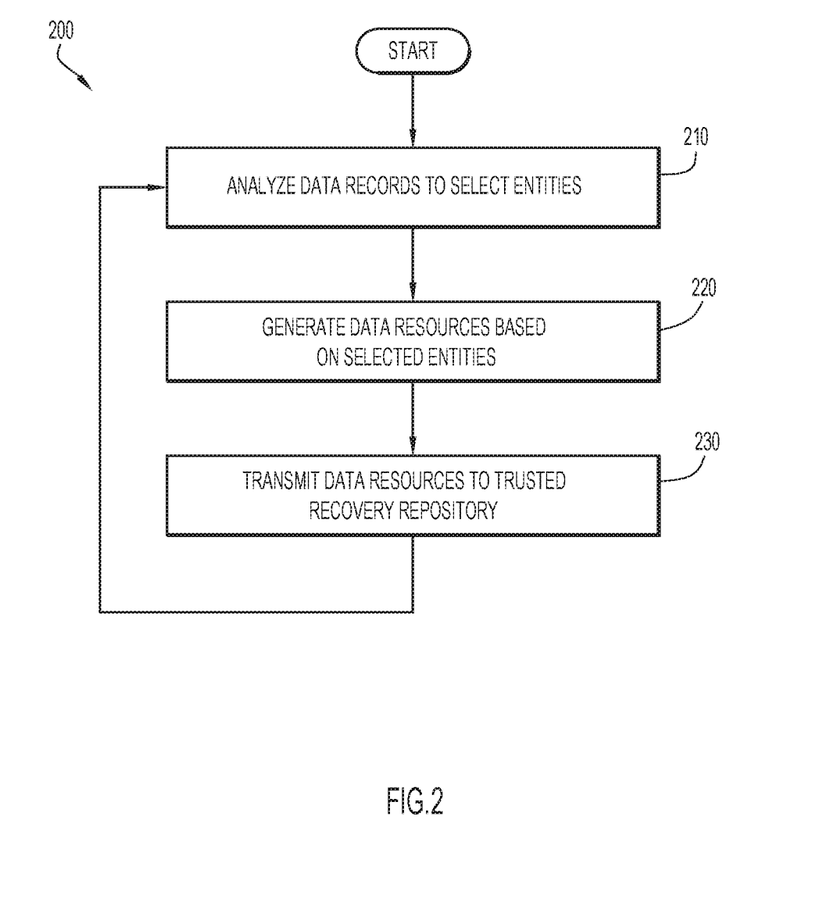
FIG. 2 is a flow chart depicting a method of maintaining a data backup for upcoming services in accordance with an embodiment of the present invention.

FIG. 2 is a flow chart depicting a method 200 of maintaining a data backup for upcoming services in accordance with an embodiment of the present invention.

Data records are analyzed to select entities at operation 210. Data records for entities being provided services, such as patients being provided health care services, are analyzed to identify in particular any entities that are scheduled to receive a service, and/or likely to receive a service, within a particular future time period. Entity selection module 130 may select entities whose records indicate that the entities are scheduled to receive a service within the time period. Additionally or alternatively, entities are selected on the basis of their data records indicating that the entities are likely to receive service within the time period. An entity that is likely to receive service can be identified using a rules-based approach to evaluate values of the entity's data record. The likelihood that a particular entity will receive service can be estimated using a trained machine learning model that estimates a probability of an entity will receive service, and any entities whose likelihood values satisfy a discrimination threshold may be selected. Thus, for example, entity selection module 130 may identify entities scheduled to receive a service within the next day, within the next week, within the next month, and the like. In some embodiments, the time period is based on a Recovery Time Objective (RTO) of a database system.

Data resources are generated based on the selected entities at operation 220. Data resource module 135 may generate a data resource for a selected entity based on the entity's data record. The data resource may store data according to a standard; for example, each data resource may be a FHIR resource. Thus, entity data may be stored in a use-case agnostic format until the data is requested. A data resource includes details such as a longitudinal patient record, demographic information, schedule or appointment information, and the like. Additionally, a data resource may include instructions to transform data from the use-case agnostic format of the data resource into one or more readable or printable forms that can be used to provide a service in the event of an infrastructure outage event. In some embodiments, data resources are encrypted, and a recovery key is generated that can be used to decrypt one or more of the data resources.

The data resources are transmitted to a trusted recovery repository at operation 230. Data resources may be transmitted as they are generated, or data resources may be transmitted upon completion of a data resource generation job. The trusted recovery repository may provide data storage in a location that is off-site from the database system. After a scheduled amount of time, another data resource generation job may be repeated to ensure that the trusted recovery repository is consistently being provided updated data. Thus, method 200 repeatedly analyzes data records to select entities at operation 210, generates data resources for those entities at operation 220, and transmits the data resources to a recovery repository at operation 230 according to a predetermined schedule.

Figure 3:
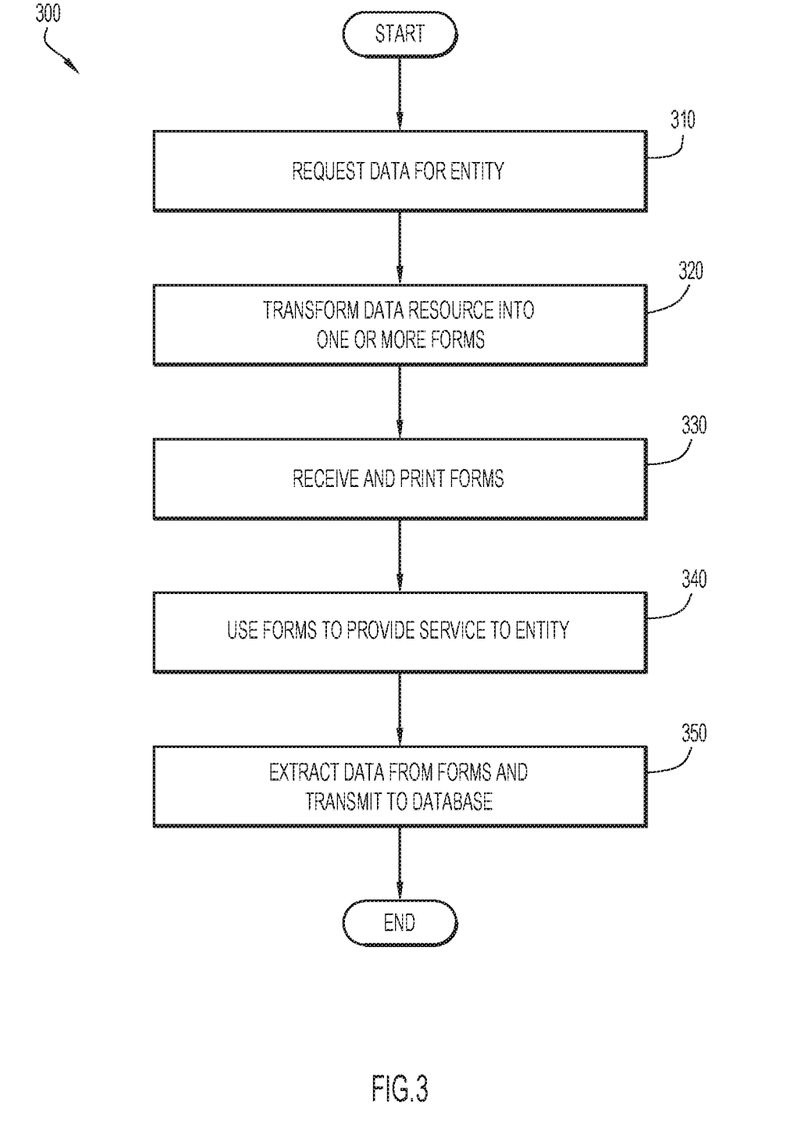
FIG. 3 is a flow chart depicting a method of providing access to data during an infrastructure outage in accordance with an embodiment of the present invention.

FIG. 3 is a flow chart depicting a method 300 of providing access to data during an infrastructure outage in accordance with an embodiment of the present invention.

Data for an entity is requested at operation 310. A provider may request data in the event that an infrastructure outage renders data on database 140 inaccessible. A provider can submit a request for data via client application 115 of client device 105. In some embodiments, the provider requests data by submitting a recovery key that has been transmitted to the provider. In some embodiments, in the event of an infrastructure outage event, a hyperlink to access entity data and a recovery key are automatically transmitted to a provider so that the provider can initiate a request for data.

A data resource is transformed into one or more forms at operation 320. Initially, recovery repository 145 may receive the recovery key submitted by a provider and use the key to decrypt a corresponding data resource. Instructions included in the data resource may be executed to transform the data resource into one or more forms. In particular, a template for each form may be populated using a mapping of data in the data record to fields of the template, thereby generating a readable, printable form. In some embodiments, a barcode or other identifier that is unique to the entity receiving the service is also inserted in each of the entity's forms. Forms may be generated in a particular sequence based on the type of service that is being provided to the entity. For example, forms for a patient who is scheduled for a series of procedures may be generated in the order of the procedures. In some embodiments, a schedule form is also generated that includes all of the services that are scheduled for the entity in the selected time period. In some embodiments, data resources are transformed into forms using a process of a requesting device, such as client device 105 or a device of provider domain 155.

Forms are received and printed at operation 330. Recovery repository 145 may transmit forms to a provider location, such as provider domain 155, that is indicated in the data resource used to generate the forms. Alternatively, the forms may be transmitted to a device of the user who initially requested the data (e.g., client device 105). In some embodiments, the forms are transmitted to printer queue 165 of provider domain 155, and the forms are either printed automatically, or upon user request. Forms may be printed at a printer of printers 160 that is indicated in the data resource, or forms may be printed at a printer specified by a user.

The forms are used to provide a service to an entity at operation 340. A provider, such as a health care provider, may use the forms to provide services to an entity, such as providing health care services to a patient. Additionally, the user may fill in other fields of the printed forms so that the entity's data record can be updated once database system 120 recovers from the outage event. For example, a health care provider might rely on data in a form to diagnose a condition in a patient, and may record the patient's current blood pressure in a form.

Data is extracted from the forms and transmitted to a database at operation 350. The data recorded in one or more forms may be extracted and uploaded to database system 120 upon recovery from the infrastructure outage event. For example, each form may be scanned or otherwise imaged, and image processing may be applied to convert handwriting to text. When each form is scanned and processed, a barcode on the form may indicate the entity associated with the form, so that the additional data can be automatically transmitted to database system 120 and provided to the entity's data record. In addition, the recovered data may be used to re-build or restore the primary database (e.g., in case of data loss, etc.), or a new database may be generated with the recovered information for use during and/or after the outage.

Figure 4:
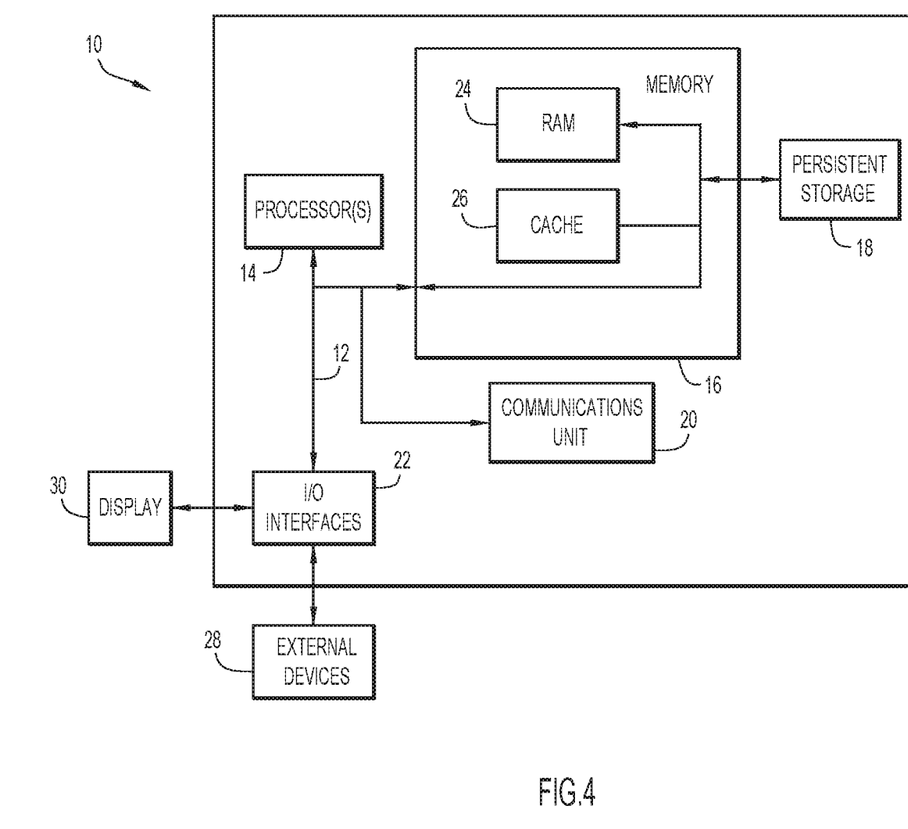
FIG. 4 is a block diagram depicting a computing device in accordance with an embodiment of the present invention.

FIG. 4 is a block diagram depicting components of a computer 10 suitable for executing the methods disclosed herein. Computer 10 may implement client device 105, database system 120, recovery repository 145, and/or devices of provider domain 155 in accordance with embodiments of the present invention. It should be appreciated that FIG. 4 provides only an illustration of one embodiment and does not imply any limitations with regard to the environments in which different embodiments may be implemented. Many modifications to the depicted environment may be made.

As depicted, the computer 10 includes communications fabric 12, which provides communications between computer processor(s) 14, memory 16, persistent storage 18, communications unit 20, and input/output (I/O) interface(s) 22. Communications fabric 12 can be implemented with any architecture designed for passing data and/or control information between processors (such as microprocessors, communications and network processors, etc.), system memory, peripheral devices, and any other hardware components within a system. For example, communications fabric 12 can be implemented with one or more buses.

Memory 16 and persistent storage 18 are computer readable storage media. In the depicted embodiment, memory 16 includes random access memory (RAM) 24 and cache memory 26. In general, memory 16 can include any suitable volatile or non-volatile computer readable storage media.

One or more programs may be stored in persistent storage 18 for execution by one or more of the respective computer processors 14 via one or more memories of memory 16. The persistent storage 18 may be a magnetic hard disk drive, a solid state hard drive, a semiconductor storage device, read-only memory (ROM), erasable programmable read-only memory (EPROM), flash memory, or any other computer readable storage media that is capable of storing program instructions or digital information.

The media used by persistent storage 18 may also be removable. For example, a removable hard drive may be used for persistent storage 18. Other examples include optical and magnetic disks, thumb drives, and smart cards that are inserted into a drive for transfer onto another computer readable storage medium that is also part of persistent storage 18.

Communications unit 20, in these examples, provides for communications with other data processing systems or devices. In these examples, communications unit 20 includes one or more network interface cards. Communications unit 20 may provide communications through the use of either or both physical and wireless communications links.

I/O interface(s) 22 allows for input and output of data with other devices that may be connected to computer 10. For example, I/O interface 22 may provide a connection to external devices 28 such as a keyboard, keypad, a touch screen, and/or some other suitable input device. External devices 28 can also include portable computer readable storage media such as, for example, thumb drives, portable optical or magnetic disks, and memory cards.

Software and data used to practice embodiments of the present invention can be stored on such portable computer readable storage media and can be loaded onto persistent storage 18 via I/O interface(s) 22. I/O interface(s) 22 may also connect to a display 30. Display 30 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

Data relating to providing access to data during infrastructure outages (e.g., data records, data resources, service data, schedule data, recovery key data, form data, etc.) may be stored within any conventional or other data structures (e.g., files, arrays, lists, stacks, queues, records, etc.) and may be stored in any desired storage unit (e.g., database, data or other repositories, queue, etc.). The data transmitted between client device 105, database system 120, recovery repository 145, and/or provider domain 155 may include any desired format and arrangement, and may include any quantity of any types of fields of any size to store the data. The definition and data model for any datasets may indicate the overall structure in any desired fashion (e.g., computer-related languages, graphical representation, listing, etc.).

Data relating to providing access to data during infrastructure outages (e.g., data records, data resources, service data, schedule data, recovery key data, form data, etc.) may include any information provided to, or generated by, client device 105, database system 120, recovery repository 145, and/or provider domain 155. Data relating to providing access to data during infrastructure outages may include any desired format and arrangement, and may include any quantity of any types of fields of any size to store any desired data. The data relating to providing access to data during infrastructure outages may include any data collected about entities by any collection mechanism, any combination of collected information, and any information derived from analyzing collected information.

The present invention embodiments may employ any number of any type of user interface (e.g., Graphical User Interface (GUI), command-line, prompt, etc.) for obtaining or providing information (e.g., data relating to providing access to data during infrastructure outages), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

It will be appreciated that the embodiments described above and illustrated in the drawings represent only a few of the many ways of providing access to data during infrastructure outages.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., communications software, server software, client application 115, entity selection module 130, data resource module 135, etc.). These systems may include any types of monitors and input devices (e.g., keyboard, mouse, voice recognition, etc.) to enter and/or view information.

It is to be understood that the software (e.g., communications software, server software, client application 115, entity selection module 130, data resource module 135, etc.) of the present invention embodiments may be implemented in any desired computer language and could be developed by one of ordinary skill in the computer arts based on the functional descriptions contained in the specification and flowcharts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flowcharts may be modified in any manner that accomplishes the functions described herein. In addition, the functions in the flowcharts or description may be performed in any order that accomplishes a desired operation.

The software of the present invention embodiments (e.g., communications software, server software, client application 115, entity selection module 130, data resource module 135, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., data relating to providing access to data during infrastructure outages). The database system may be implemented by any number of any conventional or other databases, data stores or storage structures (e.g., files, databases, data structures, data or other repositories, etc.) to store information (e.g., data relating to providing access to data during infrastructure outages). The database system may be included within or coupled to the server and/or client systems. The database systems and/or storage structures may be remote from or local to the computer or other processing systems, and may store any desired data (e.g., data relating to providing access to data during infrastructure outages).

The present invention embodiments may employ any number of any type of user interface (e.g., Graphical User Interface (GUI), command-line, prompt, etc.) for obtaining or providing information (e.g., data relating to providing access to data during infrastructure outages), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The present invention embodiments are not limited to the specific tasks or algorithms described above, but may be utilized for any number of applications in the relevant fields, including, but not limited to, processing data to identify and ensure access to any data that is relevant to providing any service, including scheduled and unscheduled services.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A computer-implemented method for providing access to data during an outage, comprising:
   analyzing a plurality of data records, stored in a database system, to identify entities whose data records indicate that a service is within an upcoming time period, wherein the plurality of records are re-analyzed according to a predetermined schedule to update the entities that are identified based on the upcoming time period;
   generating a data resource for each identified entity and storing data resources for the identified entities within a repository that is remote from the database system, wherein each data resource includes data obtained from a data record of a corresponding identified entity that is relevant to the service;
   accessing the data resource of an identified entity with a corresponding recovery key during the outage of the database system and transforming the data resource into one or more printable forms, wherein the recovery key is selected from a group of: an entity-specific recovery key, a provider-specific recovery key, and an appointment-specific recovery key; and
   transmitting the one or more printable forms to one or more providers of the service, wherein the one or more printable forms are automatically transmitted to a printing queue designated by each provider, and printed, in response to the data records becoming inaccessible.

2. The computer-implemented method of claim 1, wherein each data resource indicates a mapping of data included in the data resource to fields of the one or more printable forms, and wherein each data resource is transformed according to the mapping.

3. The computer-implemented method of claim 1, wherein the entities are further identified based on a criticality of the service being provided to each entity.

4. The computer-implemented method of claim 1, wherein the one or more printable forms are selected based on the service being provided to the identified entity.

5. The computer-implemented method of claim 1, further comprising:
  receiving additional data for the identified entity from a provider after the service has been provided, wherein the additional data relates to the service that has been provided; and
  updating the data record of the identified entity using the additional data.

6. The computer-implemented method of claim 1, wherein the service comprises a medical service, and wherein each entity comprises a patient.

7. The computer-implemented method of claim 1, wherein the data included in each data resource is encrypted and wherein the corresponding recovery key is a temporary key.

8. A computer system for providing access to data during an outage, the computer system comprising:
  one or more computer processors;
  one or more computer readable storage media;
  program instructions stored on the one or more computer readable storage media for execution by at least one of the one or more computer processors, the program instructions comprising instructions to:
  analyze a plurality of data records, stored in a database system, to identify entities whose data records indicate that a service is within an upcoming time period, wherein the plurality of records are re-analyzed according to a predetermined schedule to update the entities that are identified based on the upcoming time period;
  generate a data resource for each identified entity and store data resources for the identified entities within a repository that is remote from the database system, wherein each data resource includes data obtained from a data record of a corresponding identified entity that is relevant to the service;
  access the data resource of an identified entity with a corresponding recovery key during the outage of the database system and transform the data resource into one or more printable forms, wherein the recovery key is selected from a group of: an entity-specific recovery key, a provider-specific recovery key, and an appointment-specific recovery key; and
  transmit the one or more printable forms to one or more providers of the service, wherein the one or more printable forms are automatically transmitted to a printing queue designated by each provider, and printed, in response to the data records becoming inaccessible.

9. The computer system of claim 8, wherein each data resource indicates a mapping of data included in the data resource to fields of the one or more printable forms, and wherein each data resource is transformed according to the mapping.

10. The computer system of claim 8, wherein the entities are further identified based on a criticality of the service being provided to each entity.

11. The computer system of claim 8, wherein the one or more printable forms are selected based on the service being provided to the identified entity.

12. The computer system of claim 8, wherein the program instructions further comprise instructions to:
  receive additional data for the identified entity from a provider after the service has been provided, wherein the additional data relates to the service that has been provided; and
  update the data record of the identified entity using the additional data.

13. A computer program product for providing access to data during an outage, the computer program product comprising one or more computer readable storage media collectively having program instructions embodied therewith, the program instructions executable by a computer to cause the computer to:
  analyze a plurality of data records, stored in a database system, to identify entities whose data records indicate that a service is within an upcoming time period, wherein the plurality of records are re-analyzed according to a predetermined schedule to update the entities that are identified based on the upcoming time period;
  generate a data resource for each identified entity and store data resources for the identified entities within a repository that is remote from the database system, wherein each data resource includes data obtained from a data record of a corresponding identified entity that is relevant to the service;
  access the data resource of an identified entity with a corresponding recovery key during the outage of the database system and transform the data resource into one or more printable forms, wherein the recovery key is selected from a group of: an entity-specific recovery key, a provider-specific recovery key, and an appointment-specific recovery key; and
  transmit the one or more printable forms to one or more providers of the service, wherein the one or more printable forms are automatically transmitted to a printing queue designated by each provider, and printed, in response to the data records becoming inaccessible.

14. The computer program product of claim 13, wherein each data resource indicates a mapping of data included in the data resource to fields of the one or more printable forms, and wherein each data resource is transformed according to the mapping.

15. The computer program product of claim 13, wherein the entities are further identified based on a criticality of the service being provided to each entity.

16. The computer program product of claim 13, wherein the one or more printable forms are selected based on the service being provided to the identified entity.

17. The computer program product of claim 13, wherein the program instructions further cause the computer to:
  receive additional data for the identified entity from a provider after the service has been provided, wherein the additional data relates to the service that has been provided; and
  update the data record of the identified entity using the additional data.

* * * * *